United States Patent [19]

Marsoner et al.

[11] Patent Number: 5,160,420
[45] Date of Patent: Nov. 3, 1992

[54] ANALYZING APPARATUS

[75] Inventors: Hermann Marsoner, Steinberg; Horst Rüther, Graz, both of Austria

[73] Assignee: AVL Medical Instruments AG, Schaffhausen, Switzerland

[21] Appl. No.: 692,695

[22] Filed: Apr. 29, 1991

Related U.S. Application Data

[62] Division of Ser. No. 206,291, Jun. 14, 1988.

[30] Foreign Application Priority Data

Jun. 17, 1987 [AT] Austria ............................ 1552/87

[51] Int. Cl.$^5$ ............................................. G01N 27/26
[52] U.S. Cl. ..................................... 204/433; 204/400; 204/435
[58] Field of Search ............ 204/433, 435, 406, 129.1, 204/400

[56] References Cited

U.S. PATENT DOCUMENTS

| | | | |
|---|---|---|---|
| 4,114,527 | 12/1987 | Hofmeier et al. | 204/435 |
| 4,234,333 | 11/1980 | Ghandehari et al. | 204/129.1 |
| 4,473,458 | 8/1984 | Schwartz et al. | 204/433 |
| 4,686,011 | 8/1987 | Jäckle | 204/406 |

*Primary Examiner*—John Niebling
*Assistant Examiner*—Bruce Bell
*Attorney, Agent, or Firm*—Watson, Cole, Grindle & Watson

[57] ABSTRACT

An analyzing apparatus for the purpose of analyzing samples of body fluids, comprising a sample feeding device and a measuring channel in which measuring probes are contained. In order to attain good reproducibility and uniform conditions of treatment of the samples the measuring channel is separated by means of a valve from a storage tank communicating with the sample feeding device.

1 Claim, 2 Drawing Sheets

FIG. I

ANALYZING APPARATUS

This application is a divisional application of application Ser. No. 206,291, filed Jun. 14, 1988.

BACKGROUND OF THE INVENTION

This invention relates to an analyzing apparatus primarily designed for the purpose of analyzing samples of body fluids, which is provided with a sample feeding device and a measuring channel containing measuring probes.

DESCRIPTION OF THE PRIOR ART

Such apparatuses are used in medical laboratories, for instance, for the purpose of blood gas analysis or other analyses of liquid samples. The known apparatuses may be distinguished by the type of sample feeding device used, i.e., equipment where the liquid can only be entered through a capillary tube, and such where it is fed in by means of a syringe. In the apparatuses known it is difficult to guarantee uniform conditions of treatment for all samples, which is essential, however, if tests are to be reproducible.

SUMMARY OF THE INVENTION

It is an object of this invention to propose an analyzing apparatus of the above kind which permits a simple method of sample treatment with negligible, if any, contamination.

This is achieved by separating the measuring channel by means of a valve from a storage tank communicating with the sample feeding device.

In this way it is possible to convey any sample from the storage tank to the measuring channel, no matter how it is fed into the apparatus, while offering an easy opportunity for treatment of the samples, ideally in the storage tank, directly before entering the measuring channel.

The storage tank may be designed so as to be gas-proof and heatable, and may preferably be contained in a metal block.

This simple method will enable the individual samples to be maintained at the same temperature, or rather at a controlled temperature, before the measuring process, while preventing degassing of the samples.

In order to avoid blockage of the measuring channel, especially in blood gas analysis, the invention may provide that the cross-section, or at least the smallest dimension of the cross-section of the measuring channel, be considerably smaller than that of the storage tank, the ratio preferably being 1:3 to 1:5.

These measures help prevent coagulate from entering the measuring channel.

In a preferred variant of the invention the sample feeding device is configured as a docking unit, preferably a rotatable docking disk, one side of which carries containers for one or more buffer solutions as well as fittings for a cleansing liquid and/or solution, one or more gas feed pipes and, if required, a vacuum source and/or a sealing platelet, while its other side is provided with an inlet stub connecting to the storage tank.

Due to these simple measures the apparatus may be cleaned and calibrated easily after a given number of samples, calibration being facilitated by the fact that there is a defined concentration of gas which is already known in the storage tank, such that the influence on the test sample during its transport into the measuring channel also is known and may be minimized. Besides, the design of the apparatus itself may be kept clear and simple.

If a vacuum source is provided, it will be possible to suck off droplets remaining in the vicinity of this source and of the docking unit or docking disk, which will prevent the sample from mixing with any remains of a cleansing liquid.

By providing the docking disk with a sealing platelet, a partial vacuum is built up in the section of the apparatus between the docking disk or the inlet stub and a vacuum pump located behind the measuring channel, and a strong current of air is generated in the buffer passage and in the measuring channel by a sudden opening of the inlet stub, such that any deposits remaining there are swept off.

According to another feature of the invention a humidifier may be provided between the fitting of the gas feed pipe on the sample feeding device and the gas source, and one or several additional gases may be injected via one or several mixing valves into the pipe conveying the gas after humidification.

This will permit the sensors located in the measuring channel to remain moist even during stand-by, which will keep them operational and will prevent desiccation. The use of a mixing valve will permit calibration, for instance of a chain of gas sensors arranged in the measuring channel, with two different gases or gas mixtures in a simple way.

In order to ensure uniform conditions of temperature, another feature proposes that the pipe conveying the humidified gas be provided with a heating unit. In this way the storage tank and the measuring channel, both of which are passed through by the gas of gas mixture, may be kept at a constant temperature even during stand-by operation.

In order to facilitate cleaning of the analyzing apparatus, it may be further provided that between the valve separating the measuring channel from the storage tank or connecting it thereto and the storage tank itself, a by-pass line should open into a connecting passage linking the storage tank and the measuring channel, which line should be connected with a waste tank subject to a partial vacuum and should contain a valve through which a sample may be injected into the connecting passage.

This will enable the storage tank to be cleaned separately, the cleansing liquid entering through the sample feeding device and leaving through the by-pass line. Then the cleansing liquid may be passed through the measuring channel, which is thus cleaned.

In addition, the by-pass line and the valve located in this line will permit an individual sample to be fed into the storage tank, the valve connecting the storage tank and the measuring channel being closed during injection of the sample.

In an analyzing apparatus containing a pH measuring device and a reference electrode in the measuring channel, it may be provided according to another aspect of the invention that the reference electrode be connected with the measuring channel by means of a fine-pored diaphragm, and that a capillary tube leading up to the diaphragm be provided within the reference electrode, the latter being basically configured as a closed electrode which is connected by lines to an electrolyte tank placed at a position lower than the reference electrode, and to the waste tank.

This arrangement will prevent uncontrolled mixing of the electrolyte and the sample to be analyzed. Thus, although a small amount of the sample may enter the capillary tube to the lower hydrostatic pressure generated in the reference electrode because of the lower position of the electrolyte tank, this small amount may easily be passed back to the measuring channel through the diaphragm and drained off together with the washing liquid during a rinsing process in the measuring channel, preferably at a lower pressure. If necessary, this process may be aided by pressurizing the reference electrode.

BRIEF DESCRIPTION OF THE DRAWINGS

Following is a more detailed description of the invention as illustrated by the attached drawing, in which.

DETAILED DESCRIPTION OF THE PREFERRED EMBODIMENTS

Figure 1:
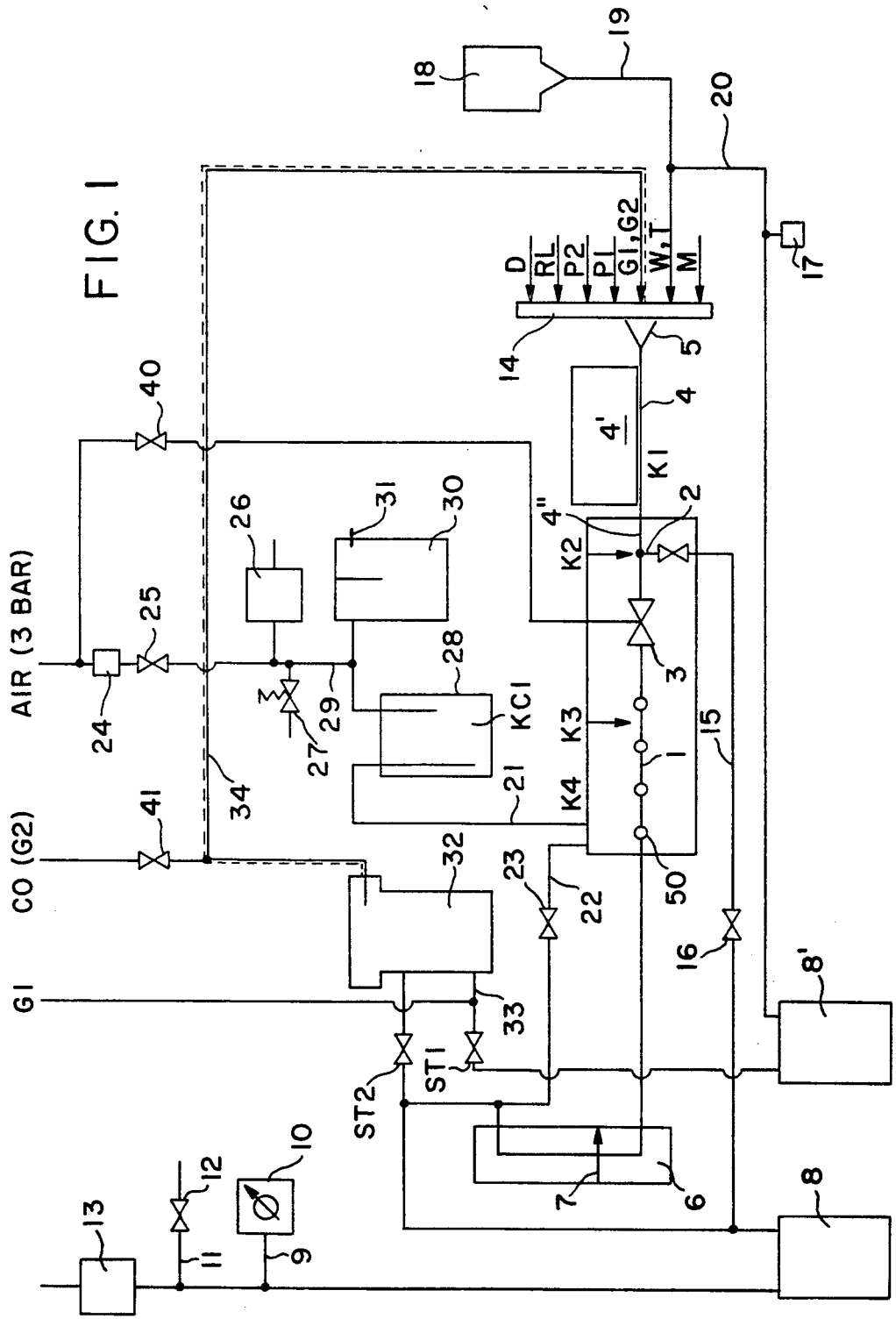
FIG. 1 is a schematic view of an analyzing apparatus as described by the invention.

The measuring channel 1 is linked to a storage tank 4 by a connecting passage 4" provided with a valve 2, at which valve a by-pass line 15 opens into the connecting passage, the storage tank 4 being contained in a metal block 4' provided with a heating unit, which makes it heatable and gas-proof. Charging of this storage tank 4 may be effected through the replaceable inlet stub 5 which is in contact with a docking disk 14, on whose other side there are arranged the samples P1, P2, fittings for a cleansing solution RL, gas feed pipes G1, G2 and for a cleansing liquid W,T and a vacuum source 18. The docking disk 14 constitutes the sample feeding device of the analyzing apparatus. By turning and docking or undocking the disk a fitting or a sample may be connected to the inlet stub 5.

On its side facing away from the sample feeding device the measuring channel 1 is connected to a hose pump 6 with a movable clamp 7, which pump 6 is connected to a vacuum-tight or vacuum-proof waste tank 8. This tank is connected to a vacuum pump 13 and, via a stub line 9, to a vacuum sensor 10.

The samples or the cleansing solution or liquid may be fed into the measuring channel 1 by sucking them in via the hose pump 6 or by injecting them into the by-pass line 15 when the valve 3 is closed, in which latter case the valve 16 must be controlled accordingly, such that the by-pass line is open towards the waste tank 8. The apparatus must be in its base state, with the vacuum pump non-operating and the waste tank 8 open to the environment.

The fitting W,T of the docking disk connects to a container 8' with a cleansing liquid, for instance water, an orifice 17 being incorporated in the respective connecting line 20, through which air may be taken in and mixed with the cleansing liquid. The process of mixing will lead to an increase in turbulences, which will improve the cleaning effect and reduce the amount of liquid required. From the connecting line 20 a stub line 19 branches off towards a vacuum tank 18.

The pneumatic valve 3 controlling the measuring channel 1 is supplied with driving air via a gas valve 40 and a suitable line.

The source of compressed air supplying the above driving air is connected by a line 29, via an orifice 24 and another gas valve 25 and a pressure relief valve 27, to a storage container 28 for the electrolyte, especially a KCl solution, and to a pressure relief nozzle 31. This pressure relief nozzle 31 is preceded by a drip catcher 30 consisting of a vessel and a baffle plate interrupting the direct passage between an inlet opening and the pressure relief nozzle 31. Furthermore, the line 29, or rather a stub line branching off therefrom, is provided with a high pressure control unit 26.

The storage container 28 is placed at a position lower than the measuring channel, which is provided with a pH measuring device whose reference electrode 50 is connected with the storage container 28 via line 21 and with the waste tank 8 via line 22. Line 22 contains a valve 23.

The gas source G1, which supplies a defined gas mixture, for instance, is connected to a humidifier 32 via a line 33, this line being connected via a valve ST1 to the water tank 8', such that the humidifier 32 may be refilled via the valve ST1. The humidifier is furthermore connected to the waste tank 8 via a valve ST2 and to the docking disk 14 via the line 34, which is provided with a heating unit, thus supplying humidified gas to the docking disk 14.

If desired, a second gas may be fed into the line 34 via the valve 41; the proportion of the additional gas, which is not humidified, preferably should be kept small, however.

The operating process is such that the sample paths which are contaminated by the sample are cleaned and dried after the measurement proper. Subsequently a calibrating gas is passed through the measuring channel 1 by putting the docking disk 14 into its proper position. This permits a one-point calibration of the gas sensors located in the measuring channel. As mentioned above, the sensors are protected from drying out by means of a continuous flow of humidified gas through the measuring channel, which is also kept up during stand-by.

By means of a control unit (not shown in this drawing) a one-point calibration of this kind may also be carried out automatically at given time intervals, calibration of the pH measuring device being effected by sucking in a buffer solution through the measuring channel by means of the hose pump 6 after suitably positioning the docking disk 14.

Besides, a suitable control program may also effect two-point calibrations at regular time intervals in essentially the same way as the one-point calibrations.

Regardless of the mode of sample entry, either via the sample feeding device, i.e., the docking disk 14, by suction, or via the by-pass line 15 by injection, valve 3 being closed, the samples are heated to a certain temperature in the storage tank 4 provided with a heater, prior to being fed into the measuring channel 1 for evaluation. The storage tank is configured as short as possible, but of sufficient length to accomodate a sufficiently large residual sample. In order to avoid blockage of the measuring channel 1 by coagulate, especially during the analysis of blood samples, the measuring channel has a cross-section considerably smaller than that of the storage tank 4 or the by-pass line 15, thus avoiding the entry of coagulate into the measuring channel.

In the analyzing apparatus described by the invention both the samples and the calibrating gas flow through the storage tank and the measuring channel, and conditions are identical for both. Due to its being exposed to the calibrating gas the sample is protected from the influence of unspecified gases which might be present in the buffer passage or in the measuring channel.

During the cleaning process the storage tank 4 is rinsed first, the washing liquid being fed via the docking disk 14 and drained via the by-pass line 15, valve 16 connecting to the waste tank. Transport of the washing liquid is ensured by the partial vacuum generated by the vacuum pump 13. In order to increase the cleaning effect, the water may be mixed with air through the orifice 17.

After the storage tank 4 has been cleaned, the cleansing liquid is sucked through the measuring channel by means of the hose pump 6, valve 16 blocking the line 15.

During the cleaning process the vacuum pump is operating and the waste tank is subject to a partial vacuum, which also acts on the vacuum tank 18 via the line 20 connecting the docking disk 14 to the water tank 8' and via the stub line 19. In this way residual drops may be sucked off from the inlet stub 5 while the vacuum pump is still operating after line 20 has been closed at the end of the cleaning process. The residual drops are sucked off via the stub line 19 and the line 20 by the vacuum established in the vacuum tank 18.

Drying of the sample paths is effected by means of an air flow generated by the vacuum pump 13, which is directed alternatingly through the by-pass line 15 and the measuring channel 1. This will also permit removal of residual drops from the area of the branch-off 2. After the rinsing process a cleansing solution may be sucked into the measuring channel to remove deposits. This operation may be repeated at certain time intervals under program control.

The unchanging positioning of the samples provided by the analyzing apparatus of the invention will greatly contribute to good reproducibility of the measured results. The samples are assessed by means of contact intervals measuring the electrical resistance of the sample. These contact intervals K1-K2, K2-K4, K3-K4 permit an assessment of the samples, or rather the sample quantities.

The sealing platelet D on the docking disk 14 permits a tight sealing of the inlet stub 5 and the establishing of a partial vacuum by means of the vacuum pump 13 in the area of the apparatus behind the docking disk 14, especially in the area of the storage tank 4 and the measuring channel 1. By quickly removing the sealing platelet D a very fast inflow of air may be achieved in this area, which will remove any deposits that may have built up.

The sample to be analyzed may also be entered by means of a capillary tube attached to the fitting M on the docking disk.

The fittings P1, P2 are used to enter buffer solutions, fittings G1, G2 are used to enter gas mixture for the purpose of calibration and for protection of the sample during transport into the measuring channel 1.

Via the fitting RL a cleansing solution and via the fitting W,T a cleansing liquid, such as water, may be entered into the storage tank 4 and the measuring channel 1; via the latter residual drops may be sucked off, thus speeding up the drying of the apparatus.

Figure 2:
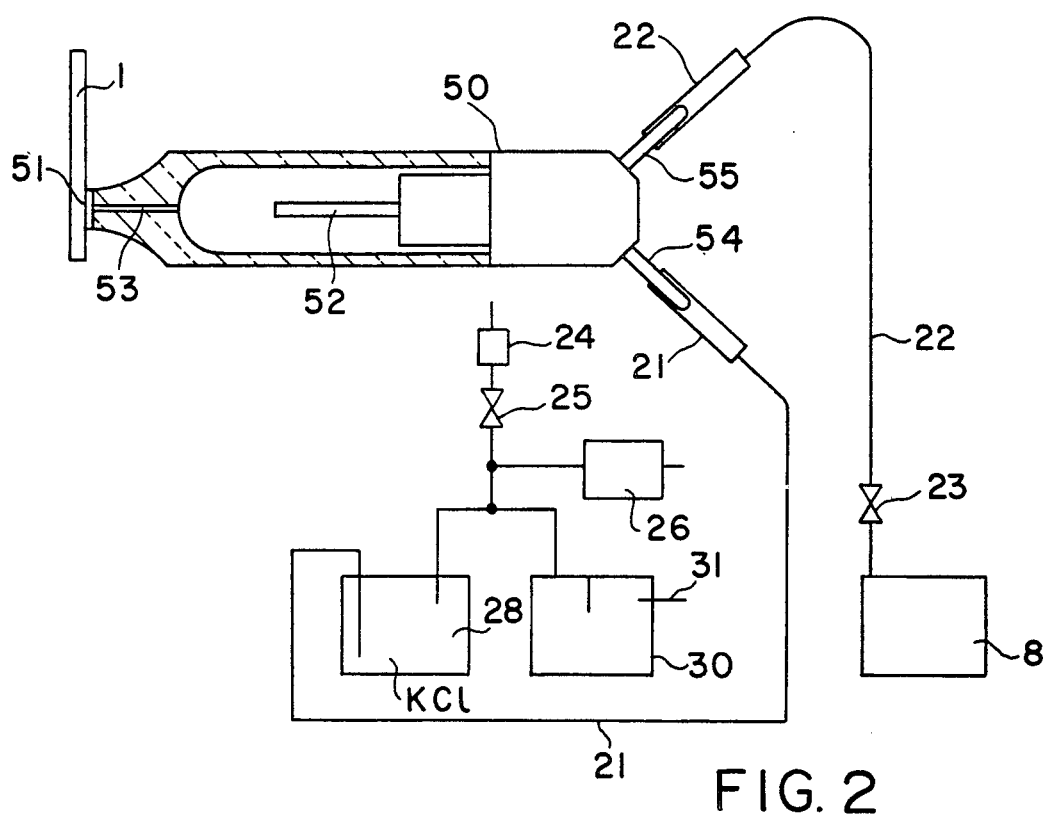
FIG. 2 shows a reference electrode for pH measurment according to the invention.

In the pH measuring device incorporated in the measuring channel a reference electrode 50 is provided, which is shown in detail in FIG. 2. Usually it contains an electrolyte bridge, preferably a KCl bridge, between the sample contained in the measuring channel 1 and the electrode 52 proper. This electrode is closed off by a fine-pored diaphragm 51, through which a small dose of KCl may be forced at the beginning of each measurement or pH calibration. Since the interior of the reference electrode is subject to a lower hydrostatic pressure during the process of measurement because of the lower position of the KCl storage tank 28, sample liquid may enter the reference electrode via the diaphragm 51. It will flow into the capillary tube 53 immediately behind the diaphragm 51, and an undesirable mixing of the electrolyte and the sample liquid is thus avoided. The sample liquid which has entered the reference electrode will leave again during the cleaning cycle, during which a partial vacuum is established in the measuring channel, and may be rinsed off.

As can be seen from FIG. 2, the reference electrode 50 represents a closed system. The upper stub 55, which is fixed in position in a manner not shown here, is connected to the waste tank 8 via the hose 22, which normally is closed off by valve 23 preferably configured as a pinch clamp. The connection via the hose 22 is only opened for a refill of the reference electrode. Hose 22 is made from gas-permeable material in order to avoid crystallisation in the area of the valve. At the same time, this hose 22 is kept as short as possible in order to minimize degassing and electrolyte consumption.

The high pressure required for transport of the electrolyte, or rather KCl, is derived from the controlled pressure of the integrated gas-mixing system, in which air pressure is applied to an orifice 24 limiting the flow. The valve 25 normally blocks the air flow such that a small amount of air is used only. As the valve is positioned behind the orifice, opening the valve 25 will result in a rapid pressure rise. If the pressure exceeds the value previously set at the high pressure control unit 26, this control unit will give off enough air to attain the preset pressure value. This pressure will propagate to the pressure-proof container 28 and further on, via line 21, to the lower stub 54 of the reference electrode 50.

If the reference electrode is to be refilled, the valve 23 is opened and transport of KCl is permitted. During pH measurement on the other hand, valve 23 remains closed during the pressure shock which will remove any sample liquid that may have entered the capillary tube 53.

The pressure relief nozzle 31 is dimensioned such that its influence during the pressure phase is negligible, but that it permits a rapid pressure drop after valve 25 has been closed, thus limiting the duration of the pressure shock.

We claim:

1. An analyzing apparatus which comprises a pH measuring device with a reference electrode, a measuring channel, a waste tank and a electrolyte tank including a means for locating said electrolyte tank below said reference electrode, said reference electrode defining a closed chamber and including a fine-pored diaphragm in communication with said measuring channel, a capillary channel which extends from said closed chamber to said fine-pored diaphragm, a first connection means for connection with said waste tank and a second connection means for connection with said electrolyte tank, said electrolyte tank generating a reduced hydrostatic pressure inside the reference electrode.

* * * * *